US008105627B2

(12) United States Patent
Volpert et al.

(10) Patent No.: US 8,105,627 B2
(45) Date of Patent: Jan. 31, 2012

(54) EXTENDED RELEASE VENLAFAXINE TABLET FORMULATION

(75) Inventors: Sima Volpert, Natania (IL); Avi Avramoff, Haifa (IL)

(73) Assignee: Dexcel Ltd., Hadera (IL)

(\*) Notice: Subject to any disclaimer, the term of this patent is extended or adjusted under 35 U.S.C. 154(b) by 1208 days.

(21) Appl. No.: 10/555,310

(22) PCT Filed: Dec. 11, 2003

(86) PCT No.: PCT/IL03/01056
§ 371 (c)(1),
(2), (4) Date: Dec. 22, 2006

(87) PCT Pub. No.: WO2004/096186
PCT Pub. Date: Nov. 11, 2004

(65) Prior Publication Data
US 2007/0082049 A1  Apr. 12, 2007

(30) Foreign Application Priority Data
May 2, 2003 (EP) .................................. 03101216

(51) Int. Cl.
*A61K 9/28* (2006.01)
(52) U.S. Cl. ........................ 424/474; 424/464
(58) Field of Classification Search .................. None
See application file for complete search history.

(56) References Cited

U.S. PATENT DOCUMENTS

| 4,535,186 | A |   | 8/1985 | Husbands et al. |         |
|-----------|---|---|--------|-----------------|---------|
| 4,601,894 | A |   | 7/1986 | Hanna et al.    |         |
| 4,657,757 | A |   | 4/1987 | Hanna et al.    |         |
| 5,283,065 | A | * | 2/1994 | Doyon et al.    | 424/467 |
| 5,451,409 | A |   | 9/1995 | Rencher et al.  |         |
| 6,217,903 | B1|   | 4/2001 | Skinner         |         |
| 6,248,363 | B1| * | 6/2001 | Patel et al.    | 424/497 |
| 6,274,171 | B1|   | 8/2001 | Sherman et al.  |         |
| 6,309,668 | B1| * | 10/2001| Bastin et al.   | 424/472 |
| 6,350,471 | B1|   | 2/2002 | Seth            |         |
| 6,703,044 | B1| * | 3/2004 | Pinhasi et al.  | 424/452 |

FOREIGN PATENT DOCUMENTS

| EP | 0797991     | 1/1997  |
|----|-------------|---------|
| EP | 1473030     | 11/2004 |
| HK | 1070821     | 1/2007  |
| IL | 120382      | 6/2003  |
| WO | WO 98/47491 | 10/1998 |
| WO | WO 01/37815 | 5/2001  |

OTHER PUBLICATIONS

De Brabander et al., J Con Relesase 89, p. 235-247, available online Apr. 16, 2003.*
"General Monographs", British Pharmacopoeia, II: 1583, 1990.
Application "Extended Release Venlafaxine Tablet Formulation", Application of 26071, Dated Aug. 8, 2007.
Hauschke et al. "A Distribution-Free Procedure for the Statistical Analysis of Bioequivalence Studies", International Journal of Clinical Pharmcol. Ther. Toxicol., 28(2): 72-78, Feb. 1990. Abstract.
Steinijans et al "Update on the Statistical Analysis of Bioequivalences Studies", International Journal of Clinical Pharmacol. Ther. Toxicol., 28(3): 105-110, Mar. 1990. Abstract.
Communication of a Notice of Opposition Dated Jul. 9, 2007 to the European Patent Office Re.: Application No. 03101216.4.
Examiner's Report Dated Dec. 4, 2008 From the Australian Government, IP Australia Re.: Application No. 2003285739.
Office Action Dated Aug. 1, 2007 From the Israeli Patent Office Re.: Application No. 159780.
Communication of a Notice of Opposition Dated Sep. 7, 2007 From the European Patent Office Re.: Application No. 03101216.4.
Communication Pursuant to Article 96(2) EPC Dated Apr. 4, 2005 From the European Patent Office Re.: Application No. 03101216.4.
European Search Report and the European Search Opinion Dated Oct. 15, 2003 From the European Patent Office Re.: Application No. 03101216.4.
International Preliminary Examination Report Dated Jun. 3, 2004 From the International Preliminary Examining Authority Re.: Application No. PCT/IL03/01056.
International Search Report Dated Mar. 12, 2004 From the International Searching Authority Re.: Application No. PCT/IL03/01056.
Opposition of Aug. 8, 2007 to European Patent EP 1473030.
Response to Opposition by Forresters Jan. 30, 2008.
"Ethylcellulose", Description, p. 195, 198-199, Handbook of Pharm. Excipients, 3rd Edition.
Lachman et al, "Tablet Coating: Tablet Properties", The Theory and Practice of Industrial Pharmacy, $3^{rd}$ Ed: 347-348, 1986, Kibbe, 2000.
"Pharmaceutical Dosage Forms", General Information, The United States Pharmacopeia, USP XXII, 1151: 1696, Jan. 1, 1990.
"Syrups / Tablets", General Monographs, British Pharmacopeia 1999, II: 1583, 1999.
Genaro, "Oral Solid Dosage Forms", The Science and Pharmacy, Remington: The Science and Practice of Pharmacy $19^{th}$ Ed., II: 1627, 1995.
Interlocutory Decision in Opposition Proceedings (Art.101(3)(a) and 106(2) EPC) Dated Dec. 17, 2009 From the European Patent Office Re. Application No. 03101216.4.
Opposition to EP 1473030 In response to the letters from Proprietor of Jul. 3, 2008 and Dec. 28, 2007, Dated Aug. 13, 2008 From the European Patent Office Re. Application No. 03101216.4.
Communication under Rule 71(3) EPC Dated Nov. 3, 2008 From the European Patent Office, Re. Application No. 04765928-219.
Lachman et al "The Theory and Practice of Industrial Pharmacy": 289, 1986.
Wyeth "American Home Products Changes Name to Wyeth, Reflecting Evolution to Global, Research-Based Pharmaceutical Company", Wyeth News and Press Release Archive, Mar. 11, 2002.

(Continued)

*Primary Examiner* — Nissa Westerberg

(57) ABSTRACT

An extended release formulation for administration of venlafaxine in an oral tablet dosage form. The formulation preferably features a core, over which an outer coating is layered. The core preferably contains venlafaxine, a filler, and a water soluble cellulosic polymer, optionally and more preferably with a water insoluble cellulosic polymer. The core is preferably coated with a coating material. The coating preferably contains a mixture of water soluble cellulosic polymer and a water insoluble cellulosic polymer. According to a first embodiment of the present invention, the filler is preferably present in an amount of at least about 40% weight per weight of the total formulation. More preferably, the filler comprises microcrystalline cellulose. Most preferably, the filler solely comprises microcrystalline cellulose. Also most preferably, microcrystalline cellulose is present in the core in a range of from about 45% to about 65% weight per weight of the total formulation.

27 Claims, 4 Drawing Sheets

OTHER PUBLICATIONS

Appeal No. T0240/10-3302, Opposition to EP-B-1473030 Dated Aug. 3, 2010 From the European Patent Office Re. Application No. 03101216.4.

Requisition by the Examiner Dated Jun. 28, 2010 From the Canadian Intellectual Property Office Re. Application No. 2,524,241.

Patent Certificate Dated May 27, 2010 From the Australian Government, IP Australia Re. Patent No. 2003285739.

Effexor "Effexor XR (Venlafaxine Hydrochloride) Extended-Release Capsules", Drug Description—Antidepressant Drugs and Medications, RxList, Sep. 18, 2007.

Motrin Motrin (Ibuprofen) Tablets, USP, Drug Information User Reviews, Side Effects, Drug Interactions and Dosage, RxList, Mar. 20, 2009.

Resp to OA of Apr. 4, 2005 as filed; July 5, 2005.

* cited by examiner

EXTENDED RELEASE VENLAFAXINE TABLET FORMULATION

RELATED PATENT APPLICATION

This application is a National Phase Application of PCT/IL03/01056 having International Filing Date of 11 Dec. 2003, which claims the benefit of European Patent Application No. 03101216.4 filed 2 May 2003. The contents of the above Application are all incorporated herein by reference.

FIELD OF THE INVENTION

The present invention is of a formulation for the extended release of venlafaxine.

BACKGROUND OF THE INVENTION

Extended release formulations for oral administration of drugs are preferred for a number of reasons. For example, they enable the patient to ingest the formulation less frequently, which may lead to increased patient compliance with the dosing regimen. They may also result in fewer side effects, as peaks and troughs of the level of the drug in the bloodstream of the patient may both be decreased, leading to a more even drug level in the blood over a period of time. Such formulations may also provide a longer plateau concentration of the drug in the blood.

Many different types of extended release formulations are known in the art. Currently, sustained and controlled release drug delivery systems administered by the oral route are usually based on either a gel forming matrix or coated formulations, or the combination thereof. The selection of the proper type of such an extended release formulation is crucial for effective drug delivery which minimizes side effects, and hence for patient compliance.

Venlafaxine, 1-[(2-dimethylamino)-1-(4-methoxyphenyl)ethyl]cyclohexanol, is an important drug in the neuropharmacological arsenal, used for the treatment of depression. Venlafaxine and the acid addition salts thereof are disclosed in U.S. Pat. No. 4,535,186, which is hereby incorporated by reference as if fully set forth herein. Venlafaxine hydrochloride may be administered to adults in compressed tablet form in doses ranging from 75 to 350 mg/day, in divided doses two or three times a day. It has been found that in therapeutic dosing with venlafaxine hydrochloride tablets, rapid dissolution results in a rapid increase in blood plasma levels of the active compound shortly after administration followed by a decrease in blood plasma levels over several hours as the active compound is eliminated or metabolized, until sub-therapeutic plasma levels are approached after about twelve hours following administration, thus requiring additional dosing with the drug. With the plural daily dosing regimen, the most common side effect is nausea, experienced by about forty five percent of patients under treatment with venlafaxine hydrochloride. Vomiting also occurs in about seventeen percent of the patients.

U.S. Pat. No. 6,274,171, issued on Aug. 14, 2001, describes one attempted solution to the problem of frequent administration of venlafaxine. The disclosure teaches an extended release formulation of spheroids, which feature an outer film coating over spheroids containing venlafaxine, and which are placed in a hard gelatine capsule. However, spheroids are a more costly and less efficient solid dosage form to produce, and also require the additional procedural step of being placed in a hard gelatin capsule.

Tablets are a less costly and a more efficient solid dosage form to manufacture, but as taught by U.S. Pat. No. 6,274,171, the production of tablets for an extended release formulation of venlafaxine does not provide satisfactory results (see column 4 lines 60-67, for example), both in terms of physical instability and too rapid dissolution.

Thus, U.S. Pat. No. 6,274,171 teaches that a formulation for venlafaxine of encapsulated spheroids is the only feasible solution for extended release.

Extended release tablet formulations are known in the art. Many of these formulations use combinations of polymers such as HPMC (hydroxypropyl methylcellulose) and ethyl cellulose. For example, U.S. Pat. No. 4,657,757 teaches the use of either HPMC alone, or a combination of HPMC and ethyl cellulose. However, the use of a filler, or of a special release controlling coating, are not taught or suggested.

U.S. Pat. No. 6,274,171 clearly teaches that an extended release formulation of venlafaxine ameliorates sharp peaks in the blood levels, which are not desired, and that in order to avoid side effects and sharp peaks in blood levels, an extended release formulation is required. However, U.S. Pat. No. 6,274,171 teaches that a tablet formulation for extended release of venlafaxine is not feasible.

U.S. Pat. No. 4,601,894 teaches that HPMC is preferably used in combination with a filler. However, it does not teach the combination of a water soluble cellulosic polymer, such as HPMC, with a water insoluble cellulosic polymer, such as ethyl cellulose. It also does not teach the use of a special release controlling coating.

U.S. Pat. No. 5,451,409 teaches that a combination of HPMC and HEC (hydroxyethyl cellulose) may be used in a sustained release formulation, but teaches that a filler, such as microcrystalline cellulose, is not suitable in combination with cellulosic polymers for a sustained release formulation. It also does not teach the use of a special release controlling coating.

U.S. Pat. No. 6,217,903 teaches the combination of two or more cellulosic polymers, but specifically teaches away from the combination of HPMC and ethyl cellulose. Also, it teaches the use of relatively low amounts of fillers, such as microcrystalline cellulose for example, of less than 30%, and typically only about 20% or less as a weight percent of the total formulation. It also does not teach the use of a special release controlling coating.

U.S. Pat. No. 6,350,471 teaches the combination of a water insoluble but water-permeable film forming polymer and a water soluble polymer, with a plasticizer, for forming a delayed release coating. However, the taught cores are immediate-release cores, or at least do not control the release characteristics of the formulation. Furthermore, it does not teach that a controlled release core would be suitable for use with the taught coating, as various deleterious effects (such as capping for example) might be expected to result.

SUMMARY OF THE INVENTION

The background art does not teach or suggest a tablet formulation for the extended release of venlafaxine.

The present invention overcomes this deficiency of the background art by providing an extended release formulation for administration of venlafaxine in a tablet form.

The formulation preferably features a core, over which an outer coating is layered. The term "core" is hereinafter defined as an uncoated tablet.

The core comprises venlafaxine, preferably with a filler, and a water soluble cellulosic polymer and more preferably with a water insoluble cellulosic polymer. The core is coated with a coating material. The coating preferably comprises a mixture of water soluble cellulosic polymer and a water insoluble cellulosic polymer.

According to a first embodiment of the present invention, the filler is preferably present in an amount of at least about 40% weight per weight of the total formulation. Unless otherwise noted, all percentages are given as percent weight per weight By "total formulation", it is meant the core and coating together; if no coating is used, then the term refers to the core alone. More preferably, the filler comprises microcrystalline cellulose. Most preferably, the filler solely comprises microcrystalline cellulose. Also most preferably, microcrystalline cellulose is present in the core in a range of from about 45% to about 65% weight per weight of the total formulation.

Preferably, the water soluble cellulosic polymer in the core is present in an amount of at least about 5% weight per weight of the total formulation. Optionally and preferably, the water soluble cellulosic polymer in the core is present in an amount of from about 5 to about 20%, weight per weight of the total formulation. More preferably, the water soluble cellulosic polymer comprises HPMC (hydroxypropyl methylcellulose). Optionally and more preferably, HPMC comprises a high molecular weight form of this polymer. By "high molecular weight", it is meant a form of HPMC having a viscosity of at least about 100 cps, and/or a form of HPMC having a molecular weight of at least about 1,000,000 g/mol. One non-limiting example of such a high molecular form of HPMC is Methocel K100M™ (Colorcon Inc., USA).

The viscosity of HPMC is proportional to molecular weight or chain length, and to concentration. A decrease in viscosity occurs with increasing temperature until the temperature has been reached where gelation takes place. Commercial designation of these products may optionally be determined by viscosity values for 2% aqueous solutions at 20° C., using a viscometer according to A.S.T.M Standards 1347-72 and D 2363-72 (American Society for Testing and Materials, Philadelphia). This method involves the use of Ubbelhode tubes, which require only a small test sample, one type for low viscosity and one for high viscosity. The viscometer is placed in a water bath at 20° C.±0.1° C. and the length of time required to deliver a given volume between index marks through a tube of specified capillary size is measured. The time in seconds is then converted to centipoise.

Solutions of HPMC are not strictly Newtonian. The shear-stress/rate-of-shear relationship is usually not linear and the viscosity behaviour is pseudoplastic with increasing shear stress i.e. their viscosity decreases with increased shear. When the viscosity of a solution is less than 500 cP, the viscosity is independent of shear and the solution may be regarded as Newtonian.

Most preferably, the water soluble cellulosic polymer in the core is present in an amount of from about 8% to about 16%, weight per weight of the total formulation.

Alternatively or additionally, the water soluble cellulosic polymer may comprise one or more of HPMC (hydroxypropyl methylcellulose), hydroxypropyl cellulose (more preferably of the high viscosity type), hydroxyethyl cellulose, polyethylene oxide, methyl cellulose, various water-soluble polysaccharides and carboxymethyl cellulose, including sodium salts thereof.

Preferably, the water insoluble cellulosic polymer in the core is present in an amount of at least about 5% weight per weight of the total formulation. More preferably, the water insoluble cellulosic polymer comprises ethyl cellulose. Most preferably, the water insoluble cellulosic polymer in the core is present in an amount of from about 5% to about 10%, weight per weight of the total formulation.

Alternatively or additionally, the water insoluble cellulosic polymer may comprise one or more of cellulose acetate and ethyl cellulose. The water insoluble cellulosic polymer, such as ethyl cellulose for example, may optionally be dry blended, or alternatively may be wet granulated with a solvent such as ethanol for example.

According to preferred embodiments of the present invention, the water soluble cellulosic polymer in the coating is present in an amount of up to about 5% weight per weight of the total formulation. More preferably, the water soluble cellulosic polymer comprises HPMC (hydroxypropyl methylcellulose). Optionally and more preferably, HPMC comprises a low molecular weight form of this polymer. By "low molecular weight" form of HPMC, it is meant a polymer preferably having a viscosity of less than about 10 cps, and more preferably less than about 5 cps, and/or a polymer having a molecular weight of less than about 10,000 g/mol. One non-limiting example of such a low molecular form of HPMC is Methocel E5™ (Colorcon Inc., USA). More preferably, the water soluble cellulosic polymer in the coating is present in an amount of from about 0.1% to about 3%, weight per weight of the total formulation, and most preferably from about 0.3% to about 1%, weight per weight of the total formulation.

Preferably, the water insoluble cellulosic polymer in the coating is present in an amount of up to about 15% weight per weight of the total formulation. More preferably, the water insoluble cellulosic polymer comprises ethyl cellulose. Most preferably, the water insoluble cellulosic polymer in the coating is present in an amount of from about 2% to about 12%, weight per weight of the total formulation. Also most preferably, ethyl cellulose in the coating is present in a range of from about 2 to about 12%, weight per weight of the entire formulation.

According to still another embodiment of the present invention, there is provided a tablet which features a core containing venlafaxine and at least about 40% of a filler, upon which core is disposed a coating, the coating featuring a mixture of a water insoluble and a water soluble cellulosic polymer, wherein the coated tablet is characterized as having a release profile of venlafaxine such that an extended release profile is obtained for venlafaxine in vivo. Surprisingly, the coated tablet provides a similar release profile to the background art encapsulated spheroid dosage form. The capability of the tablet dosage form to provide such a similar release profile is highly surprising.

Additionally, spheroids, as taught in the background art and especially as taught in U.S. Pat. No. 6,274,171, are essentially different from tablets.

The present invention preferably comprises a relatively high amount of the filler in the core. The combination of water soluble and water insoluble cellulosic polymers for both the core and the coating provides the desired bioavailability and extended release profile of the formulation according to the present invention. This combination is preferably used for a tablet dosage form, which the background art teaches is not feasible for use for an extended release formulation of venlafaxine (see for example U.S. Pat. No. 6,274,171, which clearly teaches away from such a combination in the tablet dosage form).

According to yet another embodiment of the present invention, there is provided a method for treating a subject by administering venlafaxine to the subject in need thereof, comprising administering a tablet containing venlafaxine in a core, in which the core also preferably comprises at least about 40% of a filler. The tablet also features a coating on the core, which preferably features a mixture of a water insoluble cellulosic polymer and a water soluble cellulosic polymer, wherein the tablet is characterized as having a prolonged release profile of venlafaxine in vivo.

According to another embodiment of the present invention, there is provided a coated tablet formulation, comprising: (a) a tablet core, comprising: (i) a therapeutically effective amount of venlafaxine or a pharmaceutically acceptable salt thereof; (ii) microcrystalline cellulose; (iii) HPMC (hydroxypropylmethyl cellulose) in a high molecular weight form; and (iv) ethyl cellulose; and (b) a tablet coating on the core, the coating comprising: (i) ethyl cellulose; and (ii) HPMC in a low molecular weight form.

According to still another embodiment of the present invention, there is provided a process for manufacturing a coated tablet containing venlafaxine, the process comprising: preparing a granulation of venlafaxine, HPMC, microcrystalline cellulose and ethyl cellulose, wherein an amount of the HPMC is greater than 8% weight per weight of the tablet, an amount of the microcrystalline cellulose is greater than about 40% weight per weight of the tablet, and an amount of the ethyl cellulose is greater than about 5% weight per weight of the tablet; compressing the granulation into cores; and coating the cores with a mixture of aqueous ethyl cellulose and HPMC to obtain the coated tablets.

Optionally, the process may comprise: preparing a granulation of venlafaxine, HPMC, microcrystalline cellulose and ethyl cellulose; adding a lubricant to the granulate; compressing the granulation into cores; and coating the cores with a mixture of ethyl cellulose and HPMC to obtain the coated tablets.

Also optionally, the process may comprise: mixing venlafaxine, HPMC, microcrystalline cellulose and ethyl cellulose to form a mixture; adding a lubricant to the mixture; compressing the mixture into cores; and coating the cores with a mixture of ethyl cellulose and HPMC to form the tablets.

Venlafaxine is preferably administered as venlafaxine hydrochloride, although optionally any pharmaceutically suitable form, and optionally and more preferably any pharmaceutically suitable salt, may be used. Such pharmaceutically acceptable salts thereof are disclosed for example in U.S. Pat. No. 4,535,186, which is hereby incorporated by reference as if fully set forth herein. Suitable dosage ranges are typically from about 75 mg to about 150 mg of venlafaxine base per day. All dosages given in this application, unless otherwise specified, are calculated according to the weight of venlafaxine base contained therein. For example, suitable dosage ranges of venlafaxine hydrochloride are typically from about 84.8 mg to about 169.5 mg venlafaxine hydrochloride per day, which corresponds to the dosage range given above for venlafaxine base. Preferably, the amount of venlafaxine hydrochloride, given as a percent weight per weight for the total formulation, is in a range of from about 5% to about 40%. More preferably, the amount of venlafaxine hydrochloride is in a range of from about 10% to about 30%, weight per weight. Most preferably, the amount of venlafaxine hydrochloride is about 22.5%, weight per weight.

Unless otherwise indicated, the term "venlafaxine" includes the base form and/or any pharmaceutically acceptable salt.

The tablet formulation of the present invention may optionally be used for any type of treatment for which venlafaxine and/or one of its pharmaceutically acceptable salts is recommended and/or is suitable. Uses which are known in the art include, but are not limited to, all forms of depression, either in hospital or in out-patient clinics, depressive illness with or without melancholy, depression accompanied by anxiety, depression related to aging, episodes of depression in a limited sense, especially an episode with vital symptoms, major depression, including severe episodes in hospitalized patients, new depressive episodes, panic disorder, generalized anxiety disorder-short or long-term treatment, and anxiety, including long-term treatment for melancholia.

Surprisingly, the tablet formulation of the present invention was quite effective with venlafaxine, given that the background art teaches away from the use of tablets, and instead teaches that spheroids are a suitable solid dosage form. Spheroids and tablets are quite different as taught in the background art.

BRIEF DESCRIPTION OF THE DRAWINGS

The invention is herein described, by way of example only, with reference to the accompanying drawings, wherein.

DESCRIPTION OF THE PREFERRED EMBODIMENTS

Figure 1A:
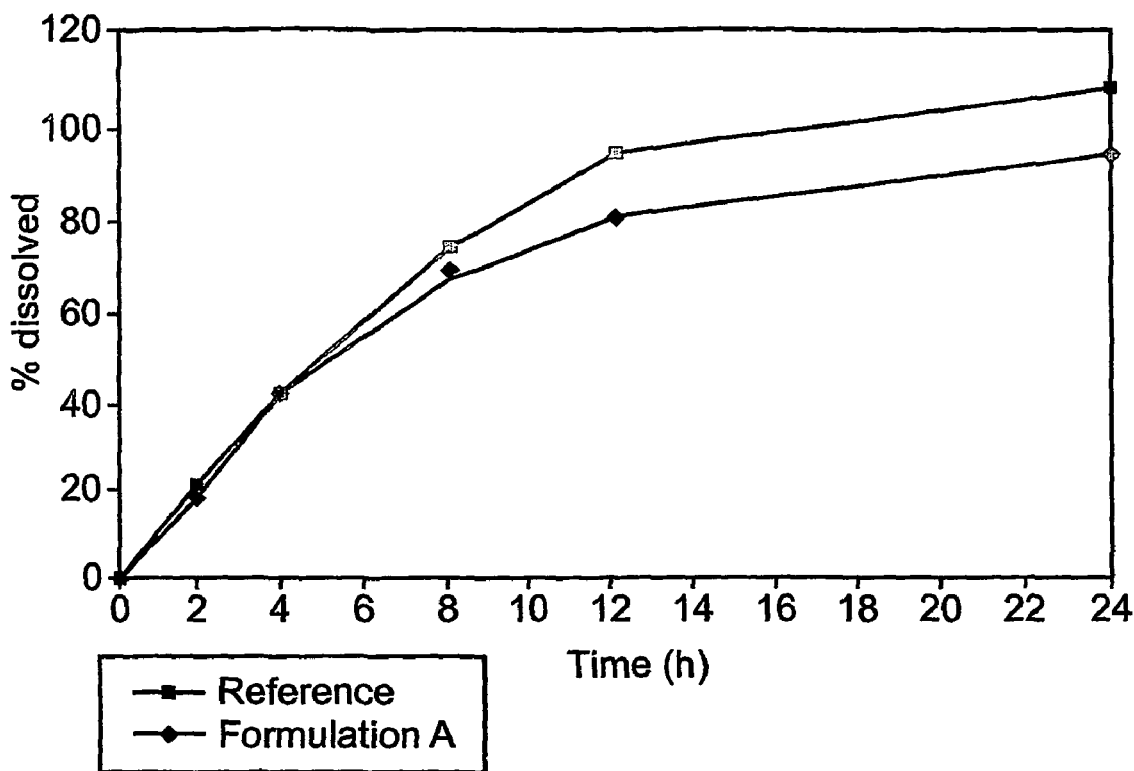
FIGS. 1A-1C show in vitro dissolution profiles of venlafaxine from different exemplary formulations according to the present invention.

The present invention is of an extended release formulation for administration of venlafaxine or a pharmaceutically acceptable salt as a tablet.

The formulation preferably features a core, over which an outer coating is layered.

The core contains venlafaxine or a pharmaceutically acceptable salt, preferably with a filler, and a water soluble cellulosic polymer, more preferably with a water insoluble cellulosic polymer. The core is preferably coated with a coating material. The coating preferably contains a mixture of water soluble cellulosic polymer and a water insoluble cellulosic polymer.

According to a first embodiment of the present invention, the filler is preferably present in an amount of at least about 40% weight per weight of the total formulation. More preferably, the filler comprises microcrystalline cellulose. Most preferably, the filler solely comprises microcrystalline cellulose. Also most preferably, microcrystaline cellulose is present in the core in a range of from about 45% to about 65% weight per weight of the total formulation.

Preferably, the water soluble cellulosic polymer in the core is present in an amount of at least about 5% weight per weight of the total formulation. More preferably, the water soluble cellulosic polymer comprises HPMC (hydroxypropyl methylcellulose). Optionally and more preferably, HPMC comprises a high molecular weight form of this polymer as previously defined. More preferably, the water soluble cellulosic polymer in the core is present in an amount of from about 5% to about 20%, weight per weight of the total formulation. Most preferably, the water soluble cellulosic polymer in the core is present in an amount of from about 8% to about 16%, weight per weight of the total formulation.

Alternatively or additionally, the water soluble cellulosic polymer may comprise one or more of HPMC (hydroxypropyl methylcellulose)hydroxypropyl cellulose (more preferably of the high viscosity type), hydroxyethyl cellulose, and carboxymethyl cellulose, including sodium salts thereof.

Preferably, the water insoluble cellulosic polymer in the core is present in an amount of at least about 5% weight per weight of the total formulation. More preferably, the water insoluble cellulosic polymer comprises ethyl cellulose. Most preferably, the water insoluble cellulosic polymer in the core is present in an amount of from about 5% to about 10%, weight per weight of the total formulation.

Alternatively or additionally, the water insoluble cellulosic polymer may comprise one or more of cellulose acetate, and ethyl cellulose.

According to preferred embodiments of the present invention, the water soluble cellulosic polymer in the coating is present in an amount of up to about 5% weight per weight of the total formulation. More preferably, the water soluble cellulosic polymer comprises HPMC (hydroxypropyl methylcellulose). Optionally and more preferably, HPMC comprises a low molecular weight form of this polymer as previously defined. More preferably, the water soluble cellulosic polymer in the coating is present in an amount of from about 0.1% to about 3%, and most preferably from about 0.3% to about 1%, weight per weight of the total formulation.

Preferably, the water insoluble cellulosic polymer in the coating is present in an amount of up to about 15% weight per weight of the total formulation. More preferably, the water insoluble cellulosic polymer comprises ethyl cellulose. Most preferably, the water insoluble cellulosic polymer in the coating is present in an amount of from about 2% to about 12%, weight per weight of the total formulation.

According to still another embodiment of the present invention, the core is preferably in a form of a tablet, and the core preferably further comprises a lubricant. The lubricant more preferably comprises magnesium stearate, which most preferably is present in an amount of up to about 2% weight per weight of the core, although optionally a concentration of from about 0.25% to about 5% weight per weight may be used. Alternatively or additionally, the lubricant may optionally be selected from the group consisting of stearate salts (magnesium, calcium, etc); stearic acid, talc, castor oil, hydrogenated palm oil, some type of starch, polyethylene glycol, sodium stearyl fumarate, compritol (glycerol behenate), waxes, or a combination thereof.

Optionally and more preferably, the core further comprises a flow regulating agent. Preferably, the flow regulating agent comprises colloidal silicon dioxide, most preferably in an amount of up to about 1%, weight per weight of the total formulation.

According to other preferred embodiments of the present invention, the coating preferably further comprises a plasticizer. More preferably, the plasticizer includes at least one of dibutyl sebacate, polyethylene glycol and polypropylene glycol, dibutyl phthalate, diethyl phthalate, triethyl citrate, tributyl citrate, acetylated monoglyceride, acetyl tributyl citrate, triacetin, dimethyl phthalate, benzyl benzoate, butyl and/or glycol esters of fatty acids, refined mineral oils, oleic acid, castor oil, corn oil, camphor, glycerol and sorbitol or a combination thereof. More preferably, the plasticizer comprises dibutyl sebacate, particularly for combination or use with ethyl cellulose. Most preferably, the plasticizer also comprises polyethylene glycol, of which a non-limiting example is Macrogol 400™ (Uniqema, USA), particularly for use or combination with HPMC. Most preferably, the plasticizer is present in an amount of up to about 5%, which is most preferably in a range of from about 0.01% to about 3% of the total formulation, percent weight per weight.

According to still another embodiment of the present invention, there is provided a tablet which features a core containing venlafaxine (base or a pharmaceutically acceptable salt thereof) and at least about 40% of a filler, upon which core is disposed a coating, the coating featuring a mixture of a water insoluble and a water soluble cellulosic polymer, wherein the tablet is characterized as providing a release profile of venlafaxine such that a therapeutically effective blood plasma concentration of venlafaxine is provided over a twenty-four period, with peak blood plasma levels of venlafaxine of no more than about 150 ng/ml.

According to yet another embodiment of the present invention, there is provided a method for treating a subject by administering venlafaxine to the subject in need thereof, comprising administering a tablet containing venlafaxine (base or a pharmaceutically acceptable salt) in a core, in which the core also contains at least about 40% of a filler. The tablet also features a coating on the core, which preferably features a mixture of a water insoluble and a water soluble cellulosic polymer. Preferably, the tablet is characterized as having the previously described release profile of venlafaxine.

The present invention is also preferably characterized according to a suitable dissolution profile. One non-limiting example of such a dissolution profile is as follows. The dissolution profile is preferably determined in USP Apparatus 1 (basket) at 100 rpm in phosphate buffer at pH 6.8 as shown in the table below:

TABLE 1

Exemplary Dissolution Profile

| Time (hours) | Average % Venlafaxine released |
|---|---|
| 2 | <30 |
| 4 | 25-45 |
| 8 | 55-75 |
| 12 | 75-95 |
| 24 | >80 |

According to an exemplary, non-limiting embodiment of the present invention, the venlafaxine formulation may optionally be manufactured as follows. This process is for manufacture with the following ingredients: core—ethyl cellulose, venlafaxine hydrochloride, microcrystalline cellulose, HPMC, colloidal silicon dioxide, and magnesium stearate; coating—polyethylene glycol, HPMC, ethyl cellulose, and dibutyl sebacate.

For manufacture of the core, ethyl cellulose is dissolved in a suitable organic solvent such as ethyl alcohol for example, to form a granulation solution. Venlafaxine hydrochloride, HPMC and microcrystalline cellulose are then mixed. The dissolved ethyl cellulose is then added to the mixture to form a granulate. The granulate is dried, for example with a fluid bed dryer. The dried granulate is then milled, and then optionally blended to form a blend.

Next, colloidal silicon dioxide and magnesium stearate are sieved. The sieved materials are preferably mixed with the previously prepared blend. The mixture is then compressed to form the tablets.

For the coating, PEG and HPMC are dissolved in water to form a solution. The solution is then added to the suspension of ethyl cellulose with dibutyl sebacate, and stirred for about 45 minutes to form the coating solution.

The previously prepared cores are then coated with the coating solution.

EXAMPLES

For the purposes of the examples below, and without any intention of being limiting, unless otherwise noted, the term "venlafaxine" refers to venlafaxine hydrochloride.

Example 1

Tests In Vitro

These examples are of illustrative implementations of the method and formulation according to the present invention. It should be noted that all examples given herein use venlafaxine hydrochloride, referred to herein as "venlafaxine" for the purpose of brevity and without any intention of being limiting. Several formulations were tested in vitro to determine the release profile, as described in greater detail below.

Briefly, dissolution of the venlafaxine tablets was tested by using the in vitro basket method (USP), in which each tablet, containing 75 mg of venlafaxine hydrochloride (calculated relative to the weight of venlafaxine base), was placed in a vessel containing 900 ml of a suitable phosphate buffer, at pH 6.8. The basket was rotated at 100 rpm. Samples were taken at 2, 4, 8, 12 and 24 hours after the tablet was placed in the basket.

The formulations tested are given in Table 2.

TABLE 2

Different formulations of venlafaxine (75 mg of base)

| Tablet content | A mg/tab | A % | B mg/tab | B % | C mg/tab | C % |
|---|---|---|---|---|---|---|
| Core: | | | | | | |
| Venlafaxine HCl | 84.85 | 22.3 | 84.85 | 18.6 | 84.85 | 21.9 |
| Microcrystalline cellulose PH 101 | 214.15 | 56.4 | 244.15 | 53.7 | 207.15 | 53.4 |
| Ethyl cellulose 100 CPS | 20 | 5.3 | 25 | 5.5 | 20 | 5.15 |
| HPMC 2208 | 30 | 7.9 | 60 | 13.2 | 37 | 9.5 |
| Colloidal Silicon Dioxide | 2.0 | 0.53 | 2.0 | 0.44 | 2.0 | 0.52 |
| Magnesium Stearate | 4.0 | 1.0 | 4.0 | 0.88 | 4.0 | 1.0 |
| Total weight uncoated tablet | 355 | 93 | 420 | 92 | 355 | 91 |
| Coating | | | | | | |
| Ethyl cellulose aqueous solution (as dried weight) | 18 | 4.7 | 25 | 5.5 | 25 | 6.4 |
| Dibutyl sebacate | 4.3 | 1.1 | 6 | 1.3 | 5.5 | 1.4 |
| HPMC 2910/5 | 2.9 | 0.76 | 4.0 | 0.88 | 1.9 | 0.5 |
| Macrogol 400 (PEG) | 0.09 | 0.02 | 0.12 | 0.03 | 0.6 | 0.15 |
| Total weight of coating | 25 | 6.6 | 35 | 7.7 | 33 | 8.5 |
| Total weight of formulation | 380 | 100 | 455 | 100 | 388 | 100 |

Figure 1B:
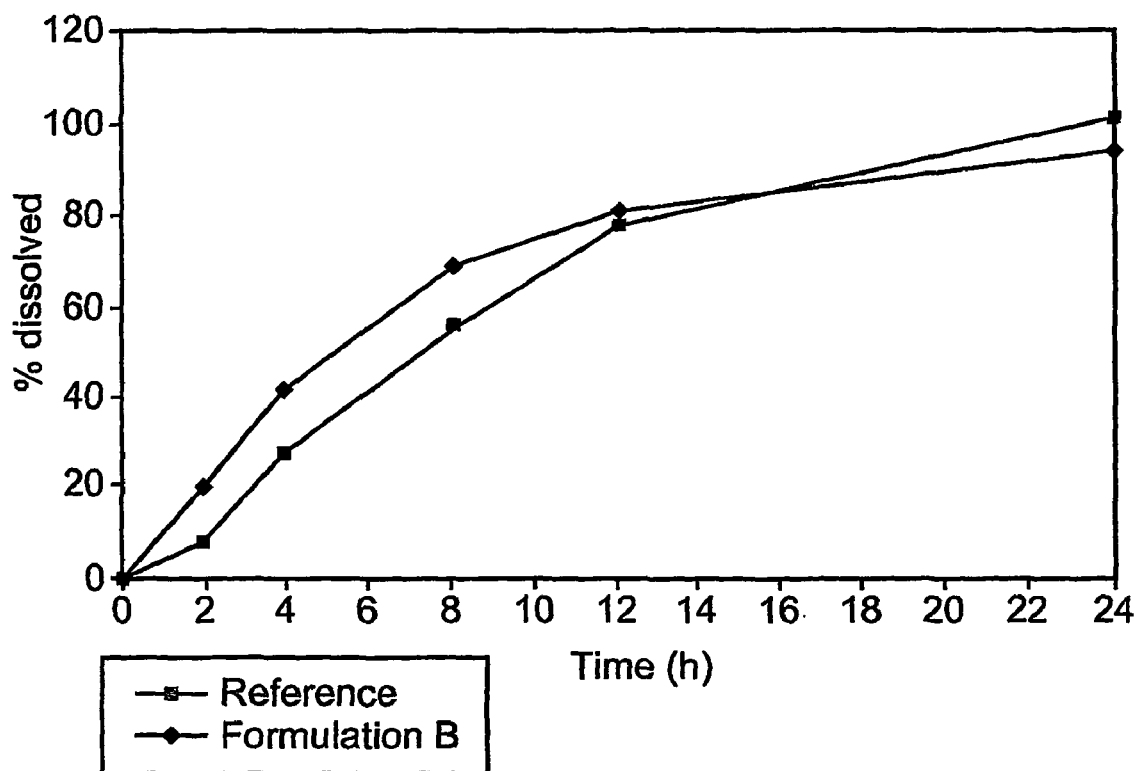
Figure 1C:
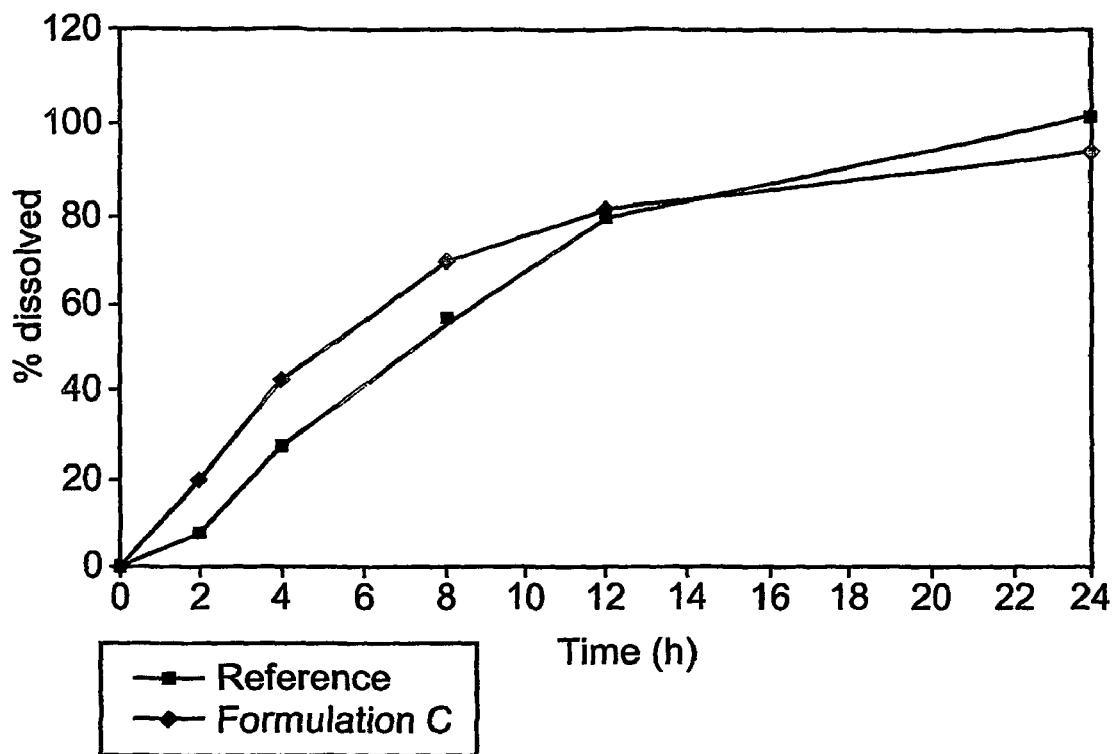

As shown in FIG. 1A with regard to formulation "A", a suitable controlled release formulation was obtained, with a suitable dissolution profile. Similar results were obtained for formulations "B" and "C", as shown in FIGS. 1B and 1C. For each of FIGS. 1A-1C, the in vitro dissolution profile is shown in comparison with the reference formulation, Effexor™ XL 75 mg capsules of Wyeth (USA).

Table 3 shows the comparative dissolution in terms of the concentration of venlafaxine hydrochloride obtained at each time point, given as the percentage of the total concentration of venlafaxine hydrochloride in the formulation.

TABLE 3

| Time (h) | Formulation A | Formulation B | Formulation C |
|---|---|---|---|
| 2 | 21 | 7 | 10 |
| 4 | 42 | 27 | 32 |
| 8 | 74 | 56 | 65 |
| 12 | 94 | 78 | 86 |
| 24 | 100 | 100 | 100 |

Figure 2:
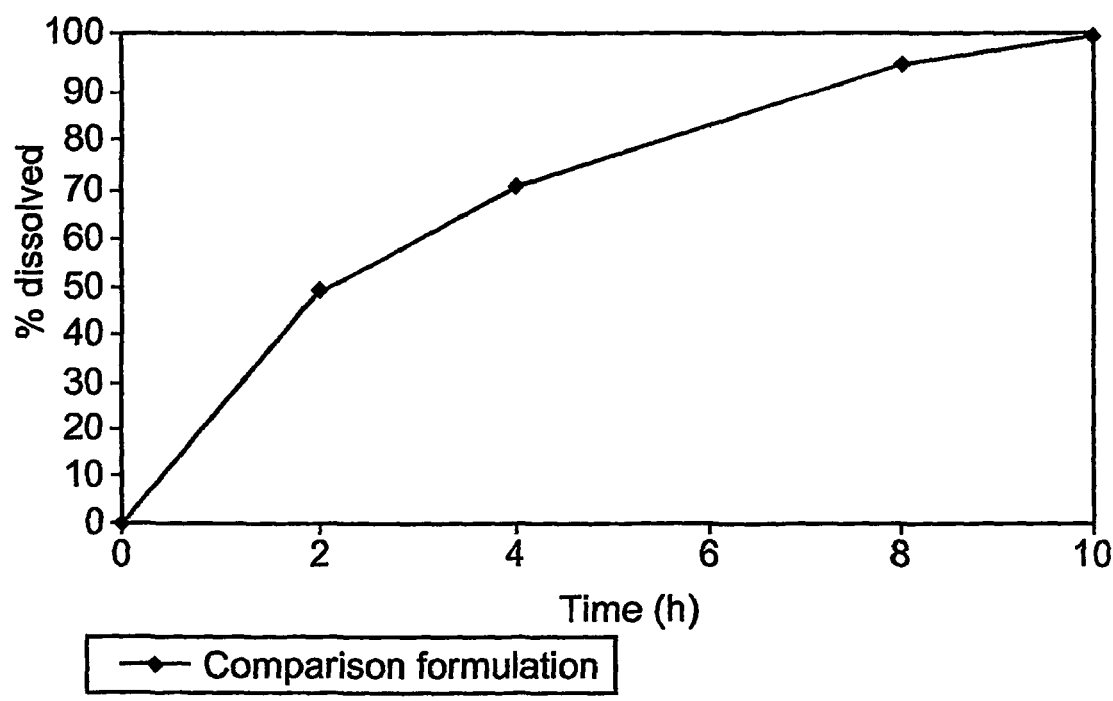
FIG. 2 shows an in vitro dissolution profile of venlafaxine from a tablet formulation that differs from the present invention.

By contrast, FIG. 2 shows the results for a tablet formulation which features an uncoated core formulation according to Table 4 (uncoated tablet formulation).

TABLE 4

| Tablet content | uncoated tablet formulation mg/tab | uncoated tablet formulation % |
|---|---|---|
| Core: | | |
| Venlafaxine HCl (75 mg of base) | 84.85 | 23.5 |
| Microcrystalline cellulose PH 101 | 244.15 | 58.1 |
| Ethyl cellulose 100 CPS | 60 | 14.2 |
| HPMC 2208 | 25 | 6.0 |
| Colloidal Silicon Dioxide | 2.0 | 0.48 |
| Magnesium Stearate | 4.0 | 1.0 |
| Total weight uncoated tablet | 420 | |

Figure 3:
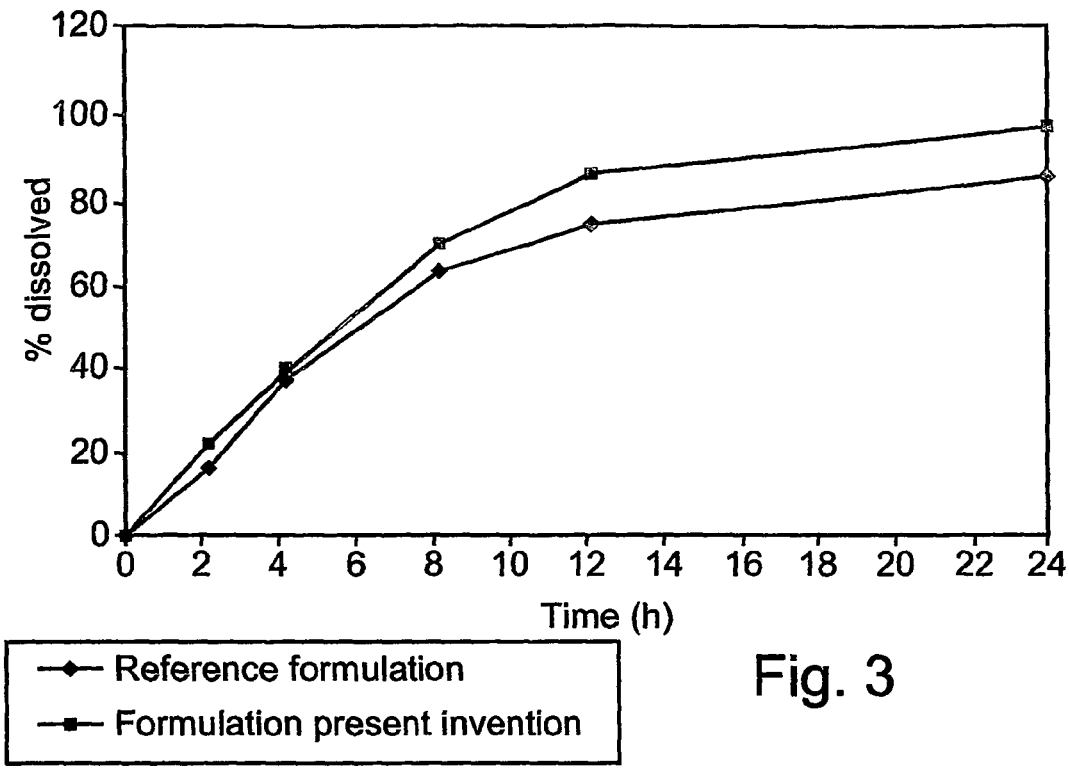
FIG. 3 shows an in vitro dissolution profile of venlafaxine according to a preferred embodiment of the present invention.

The in vitro basket results for FIG. 2 demonstrate that the dissolution profile of the uncoated tablet formulation is clearly too rapid to provide a suitable controlled release formulation, as 50% release of venlafaxine during dissolution occurs in 2 hours, while the coated tablet formulation according to the present invention preferably provides about 20% release in 2 hours, as shown in FIG. 3. Thus, the combination of the coating and the core for the formulation of the present invention provides the desired dissolution profile and is therefore important.

Example 2

Tests In Vivo

This example is of an illustrative implementation of a preferred embodiment of the formulation according to the present invention with venlafaxine. It should be noted that this example given herein uses venlafaxine hydrochloride, referred to herein as "venlafaxine" for the purpose of brevity and without any intention of being limiting. It should be noted that the tested solid dosage form contained 75 mg of venlafaxine base. The formulation was tested in vitro to determine the dissolution profile. The in vitro dissolution profile was determined as for Example 1 above, according to the formulation shown in Table 5.

TABLE 5

| Tablet content | Formulation of the present invention | |
|---|---|---|
| | mg/tab | % |
| Core: | | |
| Venlafaxine HCl | 84.85 | 22.3 |
| Microcrystalline cellulose PH 101 | 204.15 | 53.7 |
| Ethyl cellulose 100 CPS | 20 | 5.26 |
| HPMC 2208 | 40 | 10.5 |
| Colloidal Silicon Dioxide | 2.0 | 0.52 |
| Magnesium Stearate | 4.0 | 1.04 |
| Total weight uncoated tablet | 355 | 93 |
| Coating | | |
| Ethyl cellulose aqueous solution (as dried weight) | 18 | 4.73 |
| Dibutyl sebacate | 4.0 | 1.05 |
| HPMC 2910/5 | 1.9 | 0.5 |
| Macrogol 400 (PEG) | 0.6 | 0.15 |
| Total weight of coating | 24.5 | 6.6 |
| Total weight of formulation | 379.5 | 100 |

The in vitro dissolution profile is shown in FIG. 3. The results are tabulated in Table 6. As can be seen, an appropriate dissolution profile was obtained, different from those obtained by the uncoated examples.

TABLE 6

| Time (h) | Formulation of the present invention |
|---|---|
| 2 | 21 |
| 4 | 40 |
| 8 | 70 |
| 12 | 87 |
| 24 | 97 |

The in vivo release of venlafaxine from the above-referenced formulation was determined as follows. A bioequivalence study was performed in order to assess the relative bioavailability of the test product Venlafaxine 75 mg ER tablet of the present invention ("formulation of present invention"; see Table 5 above) in comparison to the reference product Effexor™ XL 75 mg capsules of Wyeth ("reference formulation"). The study was designed as a two-way randomized crossover study with a one week wash-out period. Thirty eight volunteers concluded the study. Due to a statistical outlier, one volunteer was removed from the statistical calculation for the $AUC_{(0-\infty)}$ and $AUC_{(0-t)}$.

At the start of each period, one tablet/capsule of either formulation was administered to fasting volunteers and blood samples were withdrawn according to the following schedule: 0, 1, 2, 3, 4, 5, 6, 7, 7.5, 8, 8.5, 9, 10, 12, 15, 24, 36, 48 and 60 hours post dose.

Plasma concentrations of venlafaxine and of its main metabolite O-desmethylvenlafaxine (ODV) were determined using HPLC analytical method with UV detection. The limit of quantitation (LOQ), defined as the lowest concentration determined with accuracy and run-to-run precision lower than 20% was 1.5 ng/ml.

AH values below the limit of quantitation (BLQ) were set to zero for pharmacokinetic and statistical computations A concentration-time curve was constructed for each volunteer for each period. The maximal concentration (Cmax) and the time of its occurrence (Tmax) were directly observed from the curves and the area under the curve (AUC) was computed for each volunteer.

For all parameters, the distributional properties of the residuals from the linear model were investigated directly, and after logarithmic transformation (multiplicative model). As recommended by Steinijans et al [Steinijans V. W., Hauschke D. An Update on the statistical analysis of bioequivalence studies. Int. J. Clin. Pharmacol., Ther. and Toxicol., 1989, 28(3): 105-110.], for pharmacokinetic reasons, the results of the multiplicative model are presented even when both models were found adequate. Thus, the presented ratios of AUC and Cmax are geometric means of the individual ratios.

The median values and differences between test and reference Tmax were reported and a 90% non-parametric Confidence Interval was computed by the method proposed by Hauschke et al. which does not require the restrictive assumption of an equal period effect.

CONCLUSION

The extent of absorption, as reflected by the $AUC_{(0-\infty)}$ ratio of 1.06, supports the determination of bioequivalence between the two preparations, with a 90% ANOVA Confidence Interval of 0.97→1.15. The 90% ANOVA Confidence Interval after logarithmic transformation is included in the 0.80-1.25 range.

The extent of absorption, as reflected by the $AUC_{(0-t)}$ ratio of 1.08, supports the determination of bioequivalence between the two preparations, with a 90% ANOVA Confidence Interval of 0.99→1.17. The 90% ANOVA Confidence Interval after logarithmic transformation is included in the 0.80-1.25 range.

The rate of absorption, as reflected by the Cmax values, with a ratio of 0.99, supports the determination of bioequivalence between the two preparations, with a 90% ANOVA Confidence Interval of 0.91→1.07. The 90% ANOVA Confidence Interval after logarithmic transformation is included in the 0.80-1.25 range.

The difference in Time to Maximal concentration, as reflected by the Tmax values, have the median difference estimate of 0.50 hours with a 90% nonparametric Confidence Interval of −0.25→1.25. This indicates an equivalent rate of absorption.

Conclusions for ODV Metabolite:

The extent of absorption, as reflected by the $AUC_{(0-\infty)}$ ratio of 1.08, supports the determination of bioequivalence between the two preparations, with a 90% ANOVA Confidence interval of 1.01→1.15. The 90% ANOVA Confidence Interval after logarithmic transformation is included in the 0.80-1.25 range.

The extent of absorption, as reflected by the $AUC_{(0-t)}$ ratio of 1.09, supports the determination of bioequivalence between the two preparations, with a 90% ANOVA Confidence Interval of 1.02→1.17. The 90% ANOVA Confidence Interval after logarithmic transformation is included in the 0.80-1.25 range.

The rate of absorption, as reflected by the Cmax values, with a ratio of 1.02, supports the determination of bioequivalence between the two preparations, with a 90% ANOVA Confidence Interval of 0.93→1.13. The 90% ANOVA Confidence Interval after logarithmic transformation is included in the 0.80-1.25 range.

The difference in Time to Maximal concentration, as reflected by the Tmax values, have the median difference estimate of 1.50 hours with a 90% nonparametric Confidence Interval of 0.50→2.50. This indicates an equivalent rate of absorption.

Thus, the formulation of the present invention and the reference formulation exhibit very similar pharmacokinetic profiles and should be considered as bioequivalent.

The pharmacokinetic parameters obtained in this study are presented in the following tables and figures:

TABLE 7

PHARMACOKINETIC PARAMETERS:

|  | $AUC_{(0-\infty)}$ (ng × hour/ml) (n = 37) | $AUC_{(0-t)}$ (ng × hour/ml) (n = 37) | Cmax (ng/ml) (n = 38) | Tmax (hours) (n = 38) |
|---|---|---|---|---|
| VENLAFAXINE 75 mg (present invention) | 677.56 ± 434.28 (160.10; 2085.51) | 646.65 ± 434.39 (140.09; 2029.58) | 37.80 ± 20.09 (11.11; 88.42) | 7.74 ± 2.69 (5.00; 15.00) |
| REFERENCE FORMULATION XL 75 mg (originator) | 626.40 ± 378.36 (202.46; 1868.75) | 589.23 ± 371.98 (143.71; 1785.91) | 37.46 ± 17.42 (9.96; 75.19) | 7.12 ± 1.95 (5.00; 12.00) |
| CV % (Coefficient of Variation) | 22% | 22% | 21% |  |
| RATIO* (90% ANOVA C.I.) | 1.06 (0.97; 1.15) | 1.08 (0.99; 1.17) | 0.99 (0.91; 1.07) |  |
| DIFFERENCE ESTIMATE** (range) (90% non parametric C.I.) |  |  |  | 0.50 (−7.00; 9.00) (−0.25; 1.25) |

The presented values for all pharmacokinetic parameters are mean ± SD and (range).
*The presented ratios are the geometric means of the ratios between test and the reference parameters. Parametric estimators and Parametric Confidence Intervals, based on the linear model with logarithmic transformation (multiplicative model), are given.
**The presented difference is the median difference with its corresponding range. 90% non-parametric Confidence Intervals for the median difference with its corresponding median estimate was computed by the method of Hauschke et al. [Hauschke D, Steinijans V. W., Diletti E. A distribution free procedure for the statistical analysis of bioequivalence studies, Int. J. Clin. Pharmacol., Ther. and Toxicol., 1990, 28(2): 72- 78], which does not require the restrictive assumption of equal period effect as previous methods.

TABLE 8

PHARMACOKINETIC PARAMETERS FOR ODV (metabolite;)

|  | $AUC_{(0-\infty)}$ (ng × hour/ml) (n = 37) | $AUC_{(0-t)}$ (ng × hour/ml) (n = 37) | Cmax (ng/ml) (n = 38) | Tmax (hours) (n = 38) |
|---|---|---|---|---|
| VENLAFAXINE 75 mg (present invention) | 2626.94 ± 927.52 (722.99; 4554.44) | 2521.34 ± 890.38 (695.76; 4255.25) | 92.49 ± 31.43 (30.79; 153.00) | 11.74 ± 4.05 (5.00; 24.00) |
| REFERENCE FORMULATION XL 75 mg (originator) | 2399.42 ± 745.34 (539.99; 4002.54) | 2266.02 ± 715.75 (511.43; 3702.41) | 90.62 ± 30.18 (24.63; 157.78) | 10.14 ± 2.45 (5.00; 15.00) |
| CV % (Coefficient of Variation) | 16% | 17% | 25% |  |
| RATIO* (90% ANOVA C.I.) | 1.08 (1.01; 1.15) | 1.09 (1.02; 1.17) | 1.02 (0.93; 1.13) |  |
| DIFFERENCE ESTIMATE** (range) (90% non parametric C.I.) |  |  |  | 0.50 (−6.00; 12.00) (1.50; 2.50) |

The presented values for all pharmacokinetic parameters are mean ± SD and (range).
*The presented ratios are the geometric means of the ratios between test and the reference parameters. Parametric estimators and Parametric Confidence Intervals, based on the linear model with logarithmic transformation (multiplicative model), are given.
**The presented difference is the median difference with its corresponding range. 90% non-parametric Confidence Intervals for the median difference with its corresponding median estimate was computed by the method of Hauselike et al., which does not require the restrictive assumption of equal period effect as previous methods.

Figure 4:
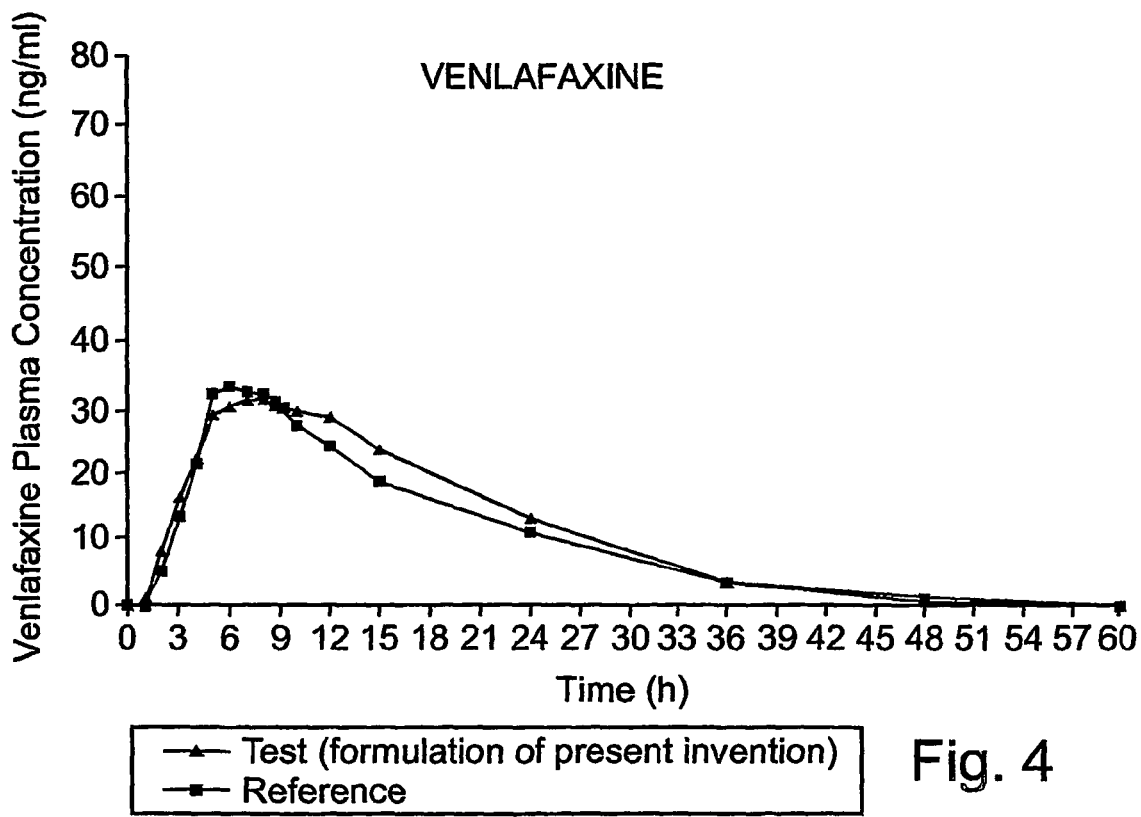
FIGS. 4-5 show in vivo release profiles of venlafaxine in the formulation according to the present invention.
Figure 5:
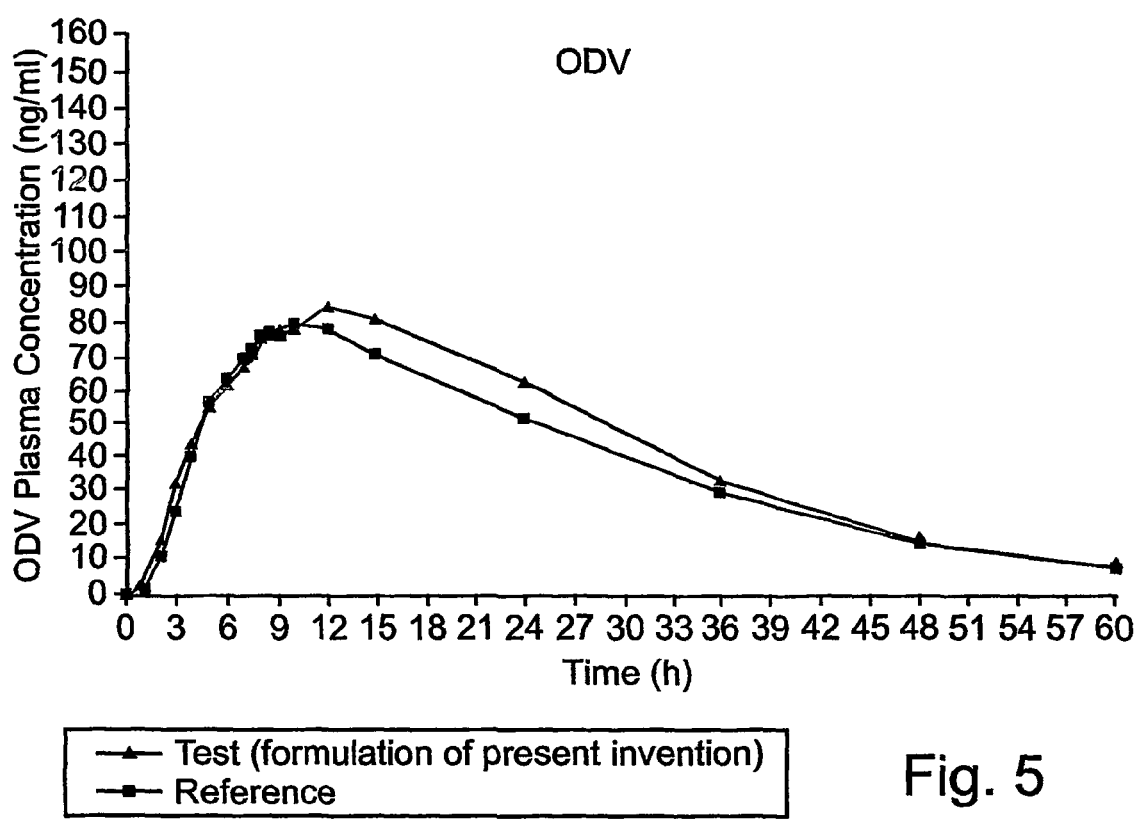

FIGS. 4 and 5 show the blood concentration values for the venlafaxine formulation according to the present invention after administration, for the formulation according to the present invention. As can be seen, the in vivo release profiles for the formulation according to the present invention and for the reference are highly similar.

What is claimed is:

1. An extended release coated tablet formulation for venlafaxine, comprising a tablet which consists of:
   (a) a core comprising a pharmaceutically effective amount of venlafaxine or a pharmaceutically acceptable salt thereof, said core being in a form of a tablet, and said core further comprising:
      (i) at least 40% of a filler, weight per weight of the entire formulation;
      (ii) at least 5% of a water soluble cellulosic polymer selected from the group consisting of hydroxypropyl methylcellulose (HPMC), hydroxypropyl cellulose, hydroxyethyl cellulose, methyl cellulose and carboxymethyl cellulose, weight per weight of the entire formulation;
      (iii) at least 5% of ethyl cellulose, weight per weight of the entire formulation;
   (b) a coating for said core, said coating comprising:
      (i) a water soluble cellulosic polymer that is hydroxypropyl methylcellulose (HPMC); and
      (ii) a water insoluble cellulosic polymer that is ethyl cellulose,
   the tablet formulation having a dissolution profile in USP Apparatus 1 (basket) at 100 rpm in phosphate buffer at pH 6.8 according to a table:

| Time (hours) | Average % Venlafaxine released |
|---|---|
| 2 | <30 |
| 4 | 25-45 |
| 8 | 55-75 |
| 12 | 75-95 |
| 24 | >80 |

2. The coated tablet of claim 1, wherein said filler is present in an amount of from about 45 to about 65%, weight per weight of the entire formulation.

3. The coated tablet of claim 2, wherein said filler comprises microcrystalline cellulose.

4. The coated tablet of claim 2, wherein said filler consists of microcrystalline cellulose.

5. The coated tablet of claim 1, wherein said water soluble cellulosic polymer in said core is present in a range of from about 5% to about 20%, weight per weight of the entire formulation.

6. The coated tablet of claim 1, wherein said HPMC in said core is present in a range of from about 8 to about 16%, weight per weight of the entire formulation.

7. The coated tablet of claim 1, wherein said HPMC in said core comprises a high molecular weight form of HPMC characterized by a viscosity of at least 100 cps in a 2% aqueous solution at 20° C.

8. The coated tablet of claim 1, wherein said water insoluble cellulosic polymer in said coating is present in an amount of up to 15%.

9. The coated tablet of claim 1, wherein said ethyl cellulose in said coating is present in a range of from about 2 to about 12%, weight per weight of the entire formulation.

10. The coated tablet of claim 1, wherein said water soluble cellulosic polymer in said coating comprises HPMC in a range of from about 0.1 to about 3%, weight per weight of the entire formulation.

11. The coated tablet claim 10, wherein said HPMC in said coating comprises a low molecular weight form of HPMC, characterized in that said HPMC has a viscosity of less than 10 cps in a 2% aqueous solution at 20° C.

12. The tablet of claim 11, wherein said HPMC has a viscosity of less than 5 cps in a 2% aqueous solution at 20° C.

13. The coated tablet of claim 1, wherein said core further comprises an excipient selected from the group consisting of a flow regulating agent, and a lubricant, or a combination thereof.

14. The coated tablet of claim 13, wherein said flow regulating agent comprises colloidal silicon dioxide in an amount of up to 1% weight per weight of said core.

15. The coated tablet of claim 13, wherein said lubricant comprises a component selected from the group consisting of magnesium stearate, stearate salts; stearic acid, talc, sodium stearyl fumarate, and glycerol behenate, or a combination thereof.

16. The coated tablet of claim 15, wherein said magnesium stearate is present in an amount of up to 2%, weight per weight of the core.

17. The coated tablet of claim 13, wherein said plasticizer comprises at least one of dibutyl sebacate, polyethylene glycol, polypropylene glycol, dibutyl phthalate, diethyl phthalate, triethyl citrate, tributyl citrate, acetylated monoglyceride, acetyl tributyl citrate, triacetin, dimethyl phthalate, benzyl benzoate, butyl and/or glycol esters of fatty acids, refined mineral oils, oleic acid, castor oil, corn oil, camphor, glycerol and sorbitol or a combination thereof.

18. The coated tablet of claim 17, wherein said plasticizer is present in a range of from about 0.01% to about 3% of the total formulation, percent weight per weight.

19. The coated tablet of claim 17, wherein said plasticizer comprises dibutyl sebacate.

20. The coated tablet of claim 19, wherein said plasticizer further comprises PEG (polyethylene glycol).

21. The coated tablet of claim 1, wherein the formulation provides a therapeutic blood plasma concentration of venlafaxine over a twenty four hour period, said blood plasma concentration of venlafaxine having a peak level of not more than 150 ng/ml.

22. A method for providing therapeutic blood plasma concentration of venlafaxine over a twenty four hour period comprising administering of a coated tablet formulation according to claim 1 to a subject.

23. The method of claim 22, wherein said venlafaxine is administered as a salt.

24. The method of claim 23, wherein said venlafaxine salt comprises venlafaxine hydrochloride.

25. The method of claim 23, wherein said venlafaxine salt is administered in the dosage range of about 75 mg to about 150 mg venlafaxine (weight determined as per venlafaxine base) per day.

26. A process for manufacturing the tablet formulation of claim 1, the process comprising:
   mixing venlafaxine, HPMC, filler and ethyl cellulose to form a mixture;
   adding a flow regulating agent and a lubricant to said mixture;
   compressing said mixture into a core; and
   coating said cores with a mixture of ethyl cellulose and HPMC to form the tablet.

27. The method of claim 22, wherein said therapeutic blood plasma concentration of venlafaxine over a twenty four hour period has a peak level of not more than 150 ng/ml.

* * * * *